US006447901B1

(12) United States Patent
Du et al.

(10) Patent No.: US 6,447,901 B1
(45) Date of Patent: Sep. 10, 2002

(54) PROCESS FOR MAKING A BREATHABLE ABSORBENT ARTICLE

(75) Inventors: Jenny G. Du, Paranaque; Ma. Luisa M. Berba, New Manila; Jose Nelson M. Conanan, Paranaque, all of (PH)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/537,557

(22) Filed: Mar. 30, 2000

Related U.S. Application Data

(60) Provisional application No. 60/128,382, filed on Apr. 8, 1999.

(51) Int. Cl.$^7$ .................................................. D02G 3/00
(52) U.S. Cl. ....................................................... 428/365
(58) Field of Search .......................................... 428/365

(56) References Cited

U.S. PATENT DOCUMENTS 5,459,193 A    10/1995    Anderson et al. ........... 524/505

FOREIGN PATENT DOCUMENTS

| EP | 0 885 942 A | 12/1998 |
| EP | 0 895 766 A | 2/1999 |

*Primary Examiner*—Edward J. Cain

(57) ABSTRACT

The present invention relates to a method of making a breathable absorbent article having a backsheet consisting essentially of a hydrophobic nonwoven material, which comprises applying positioning adhesive to the nonwoven material at a viscosity in the range of about 1000 to 1500 cps.

8 Claims, No Drawings

PROCESS FOR MAKING A BREATHABLE ABSORBENT ARTICLE

This application claims benefit of provisional application Ser. No. 60/128 382 filed Apr. 8, 1999.

The present invention provides a method of making a breathable absorbent article comprising a backsheet consisting essentially of a nonwoven material, in which positioning adhesive is applied directly to the backsheet by slot coating.

BACKGROUND OF THE INVENTION

Breathable absorbent articles, such as sanitary napkins and pantiliners, are those made with backsheets that are permeable to vapors, such as water vapor and air, and are impermeable to liquids. Such backsheets may be made of hydrophobic nonwoven materials, microporous films, or a variety of laminates. They provide the obvious advantage of improved comfort to the wearer. However, application of positioning adhesive, i.e., the adhesive applied to the garment-facing side of the backsheet to attach the absorbent article to the user's underwear, has proved to be a challenge. This is because positioning adhesives applied by typical coating methods tend to form a substantially continuous layer over the backsheet, impairing its vapor permeability and increasing subsequent transfer of the positioning adhesive to the user's underwear. This has limited the types of positioning adhesives and the methods by which they can be applied to breathable absorbent articles.

One sanitary napkin marketed in the United States and having a nonwoven backing is the Stayfree Classic, available from Personal Products Company. This sanitary napkin has a backsheet comprising a nonwoven material covering a plastic barrier. Positioning adhesive is applied to the nonwoven material in three, separated strips by slot coating. Slot coating is the continuous, direct coating of material onto a surface. During slot coating, the coating nozzle is in direct contact with the surface and a continuous stream of adhesive is extruded or pumped through the nozzle onto the receiving surface.

Positioning adhesive can also be applied to a nonwoven material by transfer coating. Positioning adhesive is coated onto a release paper and then transferred to the backsheet when the release paper is united with the absorbent article. However, even with this method subsequent transfer of the positioning adhesive to the wearer's underwear is a problem, especially since nonwoven materials are generally irregular and non-flat. Positioning adhesive, when transfer coated to the nonwoven material, remains only on the outer surfaces nonwoven material, failing to adhere to the entire surface of the nonwoven material. This leads to weak adhesive anchorage to the nonwoven material and subsequent delamination of the positioning adhesive. This is further exacerbated in absorbent articles that use vacuum formed and/or macerated pulp as the absorbent core, because the garment-facing surface of the absorbent article is macroscopically uneven and does not allow proper anchorage of positioning adhesive.

Applicant has now discovered that, unexpectedly, positioning adhesive may be directly applied to a backsheet consisting essentially of a nonwoven material by slot coating, such that the positioning adhesive forms a discontinuous layer on the nonwoven material, In this manner, both the breathability of the backsheet and the adherence of the backsheet to fabric substrates are maintained. A breathable absorbent article made according to the invention exhibits little or no positioning adhesive transfer to a user's undergarment or skin. The nonwoven backsheet has the appropriate properties to withstand direct application of positioning adhesive and offer a proper surface for receiving the positioning adhesive. An absorbent article made according to the invention also delivers better stability during use, due to reduced bunching.

SUMMARY OF THE INVENTION

The invention provides a method of making a breathable absorbent article comprising a cover, an absorbent core and a backsheet consisting essentially of a hydrophobic nonwoven material, which comprises applying positioning adhesive to the backsheet at a viscosity in the range of about 1000 to 1500 cps by slot coating.

The invention also provides a breathable absorbent article made by this method.

DETAILED DESCRIPTION OF THE INVENTION

The absorbent article may for example be a sanitary napkin, pantiliner, diaper, incontinence pad, interlabial article, or other similar product for absorbing exudates from the body, such as menses, urine, and feces. Preferably, the absorbent article is a sanitary napkin or a pantiliner. Such sanitary napkin or pantiliner may have an approximately rectangular, oval, dogbone, or peanut shape.

The absorbent article is made from a body-facing cover sheet, an absorbent core, a backsheet, and positioning adhesive. The absorbent article may comprise other known materials, layers, and additives, such as transfer layers, foam layers, net-like layers, fragrances, odor control agents, antimicrobial agents, medicaments, superabsorbents, and the like. The absorbent article may also comprise wings, tabs, or other lateral extensions as known in the art. The absorbent article can optionally be embossed with decorative designs using conventional techniques.

The absorbent core may comprise one or more layers of a variety of known absorbent materials, for example cellulose fibers, including wood pulp, regenerated cellulose fibers, and cotton fibers, polyethylene fibers, polypropylene fibers, polyester fibers, bicomponent fibers, acrylic fibers, polyvinyl alcohol fibers, peat moss and superabsorbent polymers. Combinations of these absorbent materials may be used as well. The absorbent core can be thermobonded, latex bonded, or a combination of the two, or bonded and densified in any other manner as desired.

The backsheet consists essentially of a nonwoven material. As used herein, "nonwoven material" means a fibrous, nonwoven web formed by entangling fibers of filaments, such as by spunbonding, carding or hydroentangling. A wide range of nonwoven materials are known, and any of these may be employed. Preferred nonwoven materials are made from synthetic monocomponent and/or multicomponent fibers, including polyethylene, polypropylene, polyester, and cellulose. More preferably, the nonwoven material comprising fibers selected from the group consisting of polyethylene, polypropylene, and combinations thereof.

The basis weight of the backsheet preferably ranges from about 25 to about 200 grams per square meter (gsm), more preferably from about 25 to about 60 gsm, most preferably from about 40 to 60 gsm. Generally, the backsheet has a width sufficient to cover the garment-facing side of the absorbent article. The backsheet may extend around the sides of the absorbent core in a C-shaped configuration with the portions of the backsheet that are adjacent its longitudinal edges extending upwardly from the garment-facing side toward the body-facing side of the absorbent article.

The absorbent article also comprises a liquid permeable cover formed from any fluid pervious material that is comfortable against the skin and that permits fluid to penetrate to the absorbent core. A variety of materials are known for this purpose, and any of these may be used. The cover should retain little or no fluid in its structure to provide a relatively dry surface next to the skin. The cover may comprise a nonwoven material. Alternatively, the cover may be formed from an apertured polymeric film. The thickness of the cover may vary from approximately 0.001 to 0.062 inch, depending on the material chosen. Generally, the liquid permeable cover is a single sheet of material having a width sufficient to cover the body-facing side of the absorbent article.

Positioning adhesive is applied to the garment-facing side of the backsheet, opposite the absorbent core. According to the invention, the positioning adhesive is applied by slot coating directly to the nonwoven material. The viscosity of the positioning adhesive during coating is in the range of about 1000 to 1500 cps, preferably from about 1000 to about 1200 cps. Typically, the positioning adhesive is applied at a temperature in the range of about 160 to 175° C. The basis weight of the positioning adhesive applied is preferably in the range of about 28 to 83 gsm, more preferably in the range of about 28 to about 55 gsm.

When positioning adhesive is applied to the nonwoven material in this manner, it forms a discontinuous layer on the nonwoven. It is believed the positioning adhesive flows into the crevices within the nonwoven material, penetrating the nonwoven material. This both preserves the breathability of the nonwoven material and fixes the positioning adhesive more firmly on the nonwoven material, so that transfer of the positioning adhesive to the user's undergarment is avoided.

Suitable positioning adhesives include styrenic block copolymers, polystyrene-poly(ethylene-butylene)-polystyrene block copolymers and polystyrene-polyisoprene-polystyrene block copolymer. Preferably, the positioning adhesive falls into a general class of polyarlene-polyalkene-polyarylene block co-polymers.

Equipment for slot coating of adhesives is known in the art. One useful adhesive applicator is a Nordson EP-45 applicator with a wipe nozzle.

If desired, the positioning adhesive may be applied to the backsheet in 2 to 5 or more separate lines. This further preserves the breathability of the nonwoven material.

Optionally, a release strip that has been coated on one side may be applied to protect the positioning adhesive. The coating, for example silicone, reduces adherence of the coated side of the release strip to the positioning adhesive. The release strip can be formed from any suitable sheet-like material such as paper which, when coated, adheres with sufficient tenacity to the positioning adhesive to remain in place prior to use but can be readily removed when the absorbent article is to be used.

Advantageously however, positioning adhesive that has been applied according to the invention often does not require the use of a release strip. That is, breathable absorbent articles according to the invention may be releasably affixed to themselves in the absence of a release liner (for example in a stack). Alternatively, individual absorbent articles may be bi-folded with the backsheet adhered to itself via the positioning adhesive. A user can simply unfold the article when ready to use it, without damaging it, and then place the article into her undergarment.

Should the absorbent article include wings, tabs, or other lateral extensions, such features may be folded onto and adhered to the positioning adhesive on the backsheet in the absence of any additional release strip or protective, material in between. In conventional products with wings, the wings often accidentally stick to the positioning adhesive on the backsheet while the article is being placed into a user's undergarment, and then cannot be detached without damaging the product. With the present absorbent article, the user may easily release wings that become attached to the positioning adhesive, and then wrap them around the crotch of her undergarment in the manner intended.

The following non-limiting examples further illustrate the invention.

EXAMPLE 1

A pantiliner is made according to the invention as follows. The product is a flange sealed absorbent article with a hydrophobic nonwoven backsheet. The entire pad and its absorbent core have a 2-dimensional contouring for wider coverage towards pad ends. The nonwoven backsheet is air-permeable. The components of the napkin are as follows:

Cover * 100% bicomponent (PP/PE) nonwoven fabric material, 18 gsm

Absorbent * Macerated pulp Core

Backsheet * Hydrophobic 100% PP spunbond nonwoven material, 30–100 gsm

Release * Silicone coated release paper material, 42 gsm Paper

The macerated pulp is deposited into a rotating cavity mold to form into pulp pads. These are transferred to a conveyor system, where a cover material with applied construction adhesive has already been laid. These form the cover/pulp web, which is transported by vacuum belt conveyors. Construction adhesive is applied to one side of the nonwoven backsheet and is attached to the cover/pulp web. The formed web is heat sealed around its periphery. Narrow lines of positioning adhesive are applied intermittently to formed pads with nonwoven backsheet on top of the conveyor. A continuous web of release paper is then placed on top of the nonwoven backsheet to cover the positioning adhesive. The web is then embossed and conveyed to a cutting station were pads are cut.

EXAMPLE 2

The mass transfer of positioning adhesive from a series of absorbent articles made according to the invention to a substrate was evaluated as follows.

An embossed PE film, Huntsman XP1123A, was used as the test substrate. The film was cut into a 4 in×7 in piece. The film was weighed to +/−0.001g and recorded as "Start Weight." A sanitary napkin was placed in the female side of the film with the PA side of the napkin on the film. The composite is rolled with a ten pound roller moving at a speed of 12 in/min. Using a TMI Adhesion Tester, the napkin was peeled from the film at an angle of 180° and a speed of 600 in/min. The film was then reweighed and record as "End Weight." Mass Transfer (g) of the positioning adhesive equaled the End Weight (g) minus the Start Weight (g).

The results are shown in the following table.

| Sample | Avg. Transfer* (g) | Avg. Peel (g/in) (SD) |
|---|---|---|
| 1 | No Transfer | 97.8 (27.0) |
| 2 | No Transfer | 172.4 (40.9) |
| 3 | No Transfer | 160.3 (45.9) |
| 4 | No Transfer | 232.0 (72.5) |
| 5 | No Transfer | 92.9 (15.6) |
| 6 | No Transfer | 107.5 (26.9) |
| 7 | No Transfer | 149.2 (45.6) |
| 8 | No Transfer | 178.5 (44.1) |

None of the samples showed quantitative transfer of the positioning adhesive except at the "lead" side where heavy PA had been applied. This test method was correlated to in vivo consumer responses on adhesive transfer to undergarments. The results showed that pads with no adhesive transfer in the above in vitro test had a positive consumer response in the in vivo consumer use test.

We claim:

1. A method of making a breathable absorbent article comprising a cover, an absorbent core and a backsheet consisting essentially of a hydrophobic nonwoven material, which comprises applying a positioning adhesive to the backsheet at a temperature of about 160 to 175° C. and at a viscosity in the range of about 1000 to 1500 cps by slot coating.

2. The method of claim 1, wherein the nonwoven material comprises fibers selected from the group consisting of polyethylene and polypropylene.

3. The method of claim 1, wherein the positioning adhesive is selected from the group consisting of polyarlene-polyalkene-polyarylene block co-polymers.

4. The method of claim 1, wherein the viscosity is in the range of about 1000 to 1200 cps.

5. The method of claim 1, wherein 2 to 5 separate lines of positioning adhesive are applied to the backsheet.

6. The method of claim 1, wherein the basis weight of the positioning adhesive applied is in the range of about 28 to 55 gsm.

7. The method of claim 1, wherein the breathable absorbent article has an air permeability rate of at least about 115 liters/m$^2$s.

8. A breathable absorbent article made by the process of claim 1.

* * * * *